(12) United States Patent
Biedermann et al.

(10) Patent No.: US 8,690,925 B2
(45) Date of Patent: Apr. 8, 2014

(54) LOCKING DEVICE FOR LOCKING A ROD-SHAPED ELEMENT IN A RECEIVING PART OF A BONE ANCHOR AND BONE ANCHOR WITH SUCH A LOCKING DEVICE

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/564,261

(22) Filed: Aug. 1, 2012

(65) Prior Publication Data

US 2013/0103093 A1   Apr. 25, 2013

Related U.S. Application Data

(60) Provisional application No. 61/515,635, filed on Aug. 5, 2011.

(30) Foreign Application Priority Data

Aug. 5, 2011  (EP) ..................................... 11176723

(51) Int. Cl.
*A61B 17/86* (2006.01)
*A61B 17/70* (2006.01)

(52) U.S. Cl.
USPC ............ 606/272; 606/278; 606/279; 606/328

(58) Field of Classification Search
USPC ......... 606/305, 272, 264, 265, 266, 268, 278, 606/270, 308, 328, 279
See application file for complete search history.

(56) References Cited

U.S. PATENT DOCUMENTS

| 7,204,838 B2 | 4/2007 | Jackson |
| 7,223,268 B2 | 5/2007 | Biedermann |
| 8,343,191 B2 * | 1/2013 | Matthis et al. ................ 606/264 |

(Continued)

FOREIGN PATENT DOCUMENTS

| DE | 202007012643 U1 | 12/2007 |
| EP | 1 323 391 A2 | 7/2003 |

(Continued)

OTHER PUBLICATIONS

Extended European Search Report for European Application No. 11176723.2, extended European Search Report dated Jan. 18, 2012 and mailed Jan. 30, 2012 (9pgs).

*Primary Examiner* — Pedro Philogene
(74) *Attorney, Agent, or Firm* — Christie, Parker & Hale, LLP (57) ABSTRACT

A locking device includes a first locking member including a first end, a second end, a central axis, an outer surface with an external thread, a coaxial bore, and an internal thread provided along at least a portion of the bore, and a second locking member including a first end, a second end, and an outer surface with an external thread. When the second locking member is positioned in the first locking member, the second locking member is movable along the central axis by rotating the second locking member. Movement of the second locking member is limited towards the first end of the first locking member by a first stop and towards the second end of the first locking member by a second stop, where at least one of the first stop or second stop is arranged in the bore of the first locking member.

28 Claims, 10 Drawing Sheets

(56) References Cited

U.S. PATENT DOCUMENTS

| | | |
|---|---|---|
| 2003/0125741 A1 | 7/2003 | Biedermann et al. |
| 2004/0158247 A1 | 8/2004 | Sitiso et al. |
| 2005/0171537 A1 | 8/2005 | Mazel et al. |
| 2007/0118123 A1 | 5/2007 | Strausbaugh et al. |
| 2009/0204155 A1* | 8/2009 | Aschmann .................... 606/264 |
| 2009/0318969 A1* | 12/2009 | Matthis et al. ................ 606/254 |
| 2010/0262195 A1 | 10/2010 | Jackson |

FOREIGN PATENT DOCUMENTS

| | | |
|---|---|---|
| EP | 1 935 358 A1 | 6/2008 |
| EP | 2 135 574 A1 | 12/2009 |
| EP | 2 160 988 A1 | 3/2010 |
| WO | WO 2007/075454 A1 | 7/2007 |

* cited by examiner

LOCKING DEVICE FOR LOCKING A ROD-SHAPED ELEMENT IN A RECEIVING PART OF A BONE ANCHOR AND BONE ANCHOR WITH SUCH A LOCKING DEVICE

CROSS-REFERENCE TO RELATED APPLICATION(S)

The present application claims the benefit of U.S. Provisional Patent Application Ser. No. 61/515,635, filed Aug. 5, 2011, the contents of which are hereby incorporated by reference in their entirety, and claims priority to European Patent Application EP 11 176 723.2, filed Aug. 5, 2011 the contents of which are hereby incorporated by reference in their entirety.

BACKGROUND

1. Field of the Invention

The invention relates to a locking device for securing a rod-shaped element in a receiving part of a bone anchor and to a bone anchor with such a locking device. The locking device includes a first locking element and a second locking element that is positionable in the first locking element and that is protected against backing out or unintended removal from the first locking element. The invention is particularly applicable to a polyaxial bone screw, where a head of a screw element and the rod-shaped element can be fixed independently from one another.

2. Description of Related Art

A polyaxial bone screw wherein the head of the screw element and the rod can be fixed independently is known, for example, from U.S. Pat. No. 7,223,268 B2. The locking device described therein has a first locking element cooperating with a thread provided at the inner wall of the receiving part and a second locking element in the form of a set screw that is contained in the first locking element.

A nested fastener and set screw combination for securing a spinal fixation rod to a bone screw, is described in U.S. Pat. No. 7,204,838 B2. The fastener base has a central threaded bore to receive a threaded set screw. The fastener base is provided with a radially inwardly extending abutment shoulder to engage and abut the set screw, prohibiting advancement of the set screw out of a top of the fastener and allowing for a simultaneous removal of the set screw and the fastener.

SUMMARY

It is an object of the invention to provide an improved locking device, and a bone anchor with such a locking device, that exhibits enhanced safety during manipulation in the course of a surgery.

In the locking device, a second locking element is contained or held in a first locking element in such a way that the second locking element is not separable from the first locking element during use. Therefore, if an operating error with regard to an instrument for inserting the locking device or other occurrence happens, or when the second locking element is loosened again during further adjustments of a position of a rod, the second locking element will not escape or fall out of the first locking element and therefore cannot get lost.

In some cases, the locking device according to embodiments of the invention can be delivered in a pre-assembled manner. Because the second locking element is contained in the first locking element in a manner protected against backing out or loss, handling during surgery is more effectively facilitated and security is enhanced.

Although the locking device according to embodiments of the invention is particularly applicable to a polyaxial bone anchor that is configured to allow independent head and rod fixation, it can also be used with monoaxial bone anchors, with bone plates having bone screws with variable angle placement, or with other devices.

BRIEF DESCRIPTION OF THE DRAWINGS

Further features and advantages of the invention will become apparent from the description of embodiments by means of the accompanying drawings. In the drawings:

FIG. 12b shows an enlarged portion of FIG. 12a;

FIG. 13b shows an enlarged portion of FIG. 13a;

FIG. 34a shows a cross-sectional view of a locking device according to the further modified embodiment;

FIG. 34b shows an enlarged portion of FIG. 34a;

FIG. 35a shows another cross-sectional view of the locking device according to the further modified embodiment; and FIG. 35b shows an enlarged portion of FIG. 35a.

DETAILED DESCRIPTION

Figure 1:
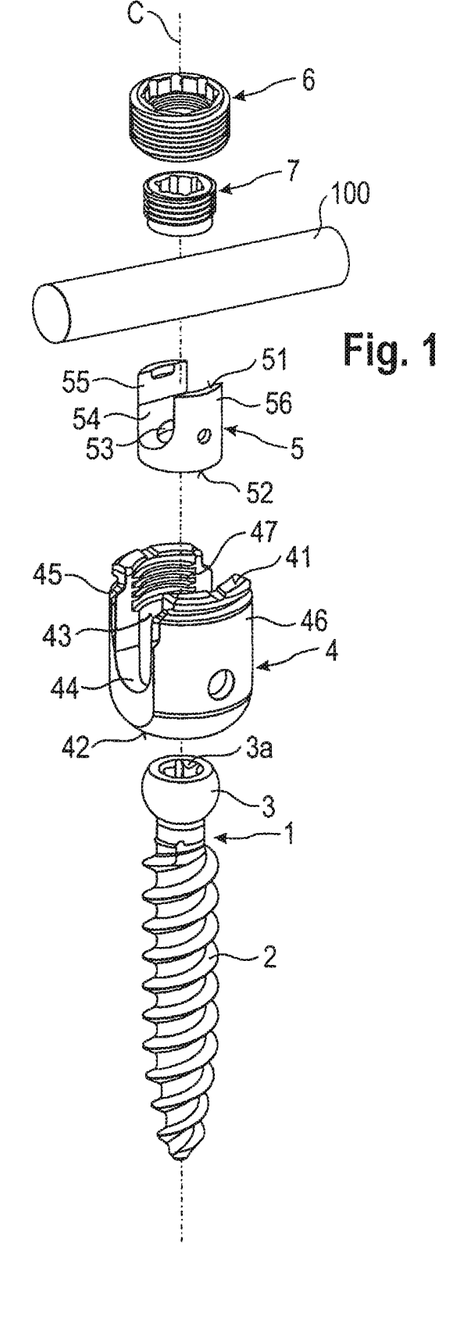
FIG. 1 shows a perspective exploded view of an embodiment of a polyaxial bone screw with a first embodiment of a locking device.
Figure 2:
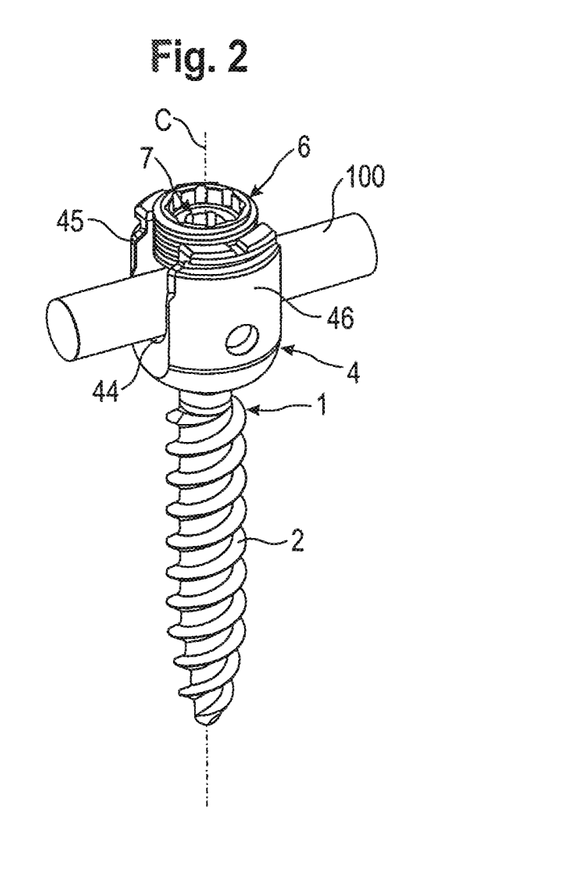
FIG. 2 shows a perspective view of the polyaxial bone screw with the locking device of FIG. 1 in an assembled state.

An embodiment of a polyaxial bone screw or bone anchor is shown in FIGS. 1 and 2. The polyaxial bone screw includes a screw element 1 with a threaded shank 2 and a head 3. The head 3 has the shape of a segment of a sphere and has at its free end a recess 3a for engagement with a screwdriver. The screw element 1 is pivotably held in a receiving part 4. The receiving part 4 is substantially cylindrical with a first end 41 and a second end 42, and a seat for the head 3 near the second end 42, which will be described later. A coaxial bore 43 extends from the first end 41 in the direction of the second end 42. Furthermore, a U-shaped recess 44 is provided at the first end 41, by means of which two free legs 45, 46 are formed. An internal thread 47 is provided at an inner wall of said legs 45, 46. The U-shaped recess 44 and the legs 45, 46 form a channel for receiving a rod 100. A pressure element 5 is provided that is configured to exert pressure onto the head 3 for locking the head 3 in a particular angular orientation of the screw element 1 relative to the receiving part 4. The pressure element 5 is substantially cylindrical with a first end 51 and an opposite second end 52, a coaxial bore 53, and a U-shaped recess 54 extending from the first end 51 into the direction of the second end 52. By means of the U-shaped recess 54, two free legs 55, 56 are formed that also form a channel for receiving the rod 100. A height of the legs 55, 56 in the embodiment shown is greater than a diameter of the rod 100, so that the legs 55, 56 extend above the rod 100 when the rod 100 is inserted.

The bone anchor further includes a locking device, which includes a first locking element 6 and a second locking element 7. In an assembled state, the second locking element 7 is nested within the first locking element 6, and is movable between a first position and a second position in an axial direction along a central axis C.

Figure 3:
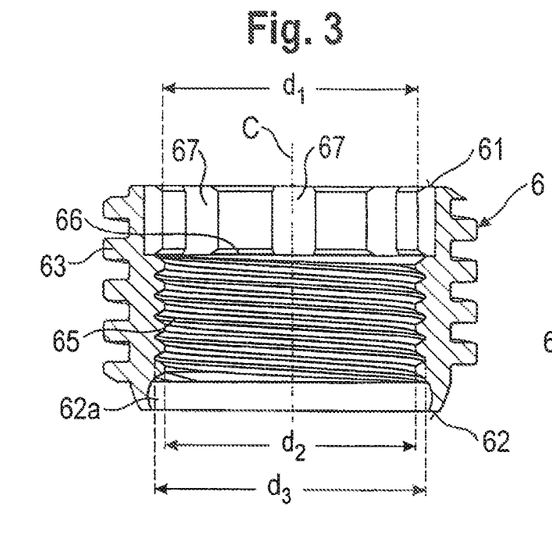
FIG. 3 shows a cross-sectional view of a first locking element of the locking device according to the first embodiment, the section being taken along a plane containing a central axis.
Figure 4:
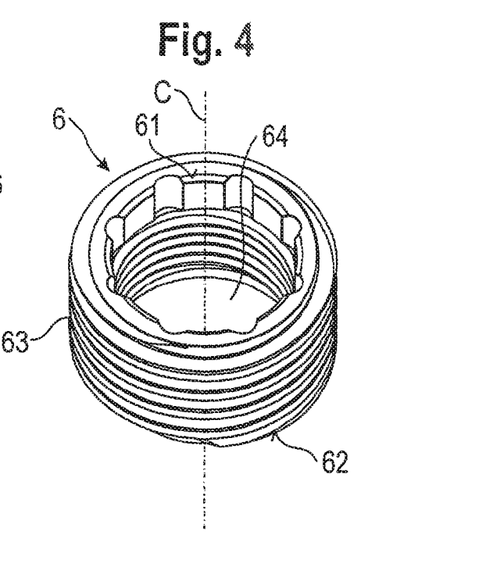
FIG. 4 shows a perspective view from a top of the first locking element of FIG. 3.
Figure 5:
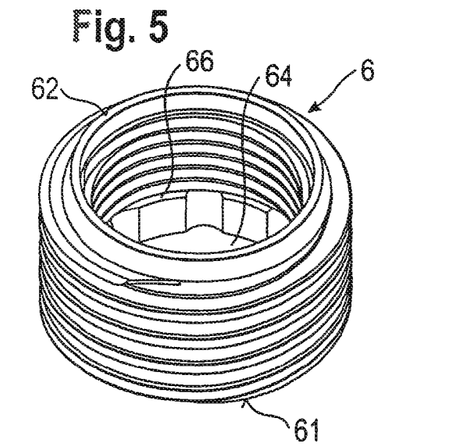
FIG. 5 shows a perspective view from a bottom of the first locking element of FIG. 3.

The locking device according to the first embodiment will now be described in more detail with reference to FIGS. 3 to 11. FIGS. 3 to 5 show the first locking element 6 before assembly with the second locking element 7. The first locking element 6 is substantially cylindrical and has a first end 61 and a second end 62. At least a portion of an outer surface of the first locking element 6 includes an external thread 63 that is configured to cooperate with the internal thread 47 provided on the legs 45, 46 of the receiving part 4. The first locking element 6 is provided with a coaxial bore 64 with a bore axis C, and a portion 65 including an internal thread. The portion 65 is adjacent or near the second end 62 and extends up to a distance from the first end 61. A thread form of the external thread 63 is preferably a thread form that prevents splaying of the legs 45, 46 of the receiving part 4, such as a flat thread (as shown) or a negative angle thread with a negative angle of a load-bearing surface. The internal thread can have any thread form, such as a metric thread as shown for example in FIGS. 9 to 11, and can alternatively have a flat thread.

The first locking element 6 further includes at the second end 62 a threadless concavely rounded hollow cylindrical portion 62a that can be, after insertion of the second locking element 7, bent inwards as described below. Adjacent the first end 61, the coaxial bore has an inner diameter $d_1$ that is the same or smaller than an inner diameter $d_2$ measured between the crests of the thread of the internally threaded portion 65, and smaller than a diameter $d_3$ between the thread roots of the internally threaded portion 65. By means of this, a stop in the form of an abutment 66 is provided for stopping advancement of the second locking element 7 in the direction of the first end 61 of the first locking element 6. Adjacent the first end 61, an engagement structure 67 for engagement with a tool is also provided. The engagement structure 67 can be a plurality of semi-spherical grooves arranged around the axis C.

Figure 6:
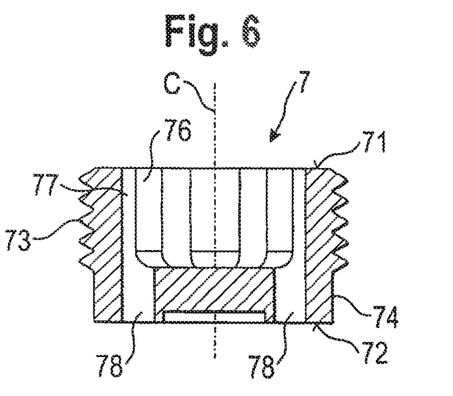
FIG. 6 shows a cross-sectional view of a second locking element of the locking device according to the first embodiment, the section taken along a plane containing a central axis.
Figure 7:
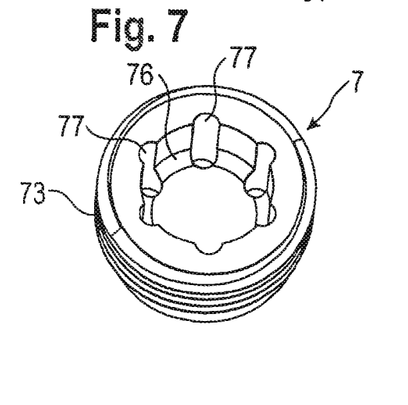
FIG. 7 shows a perspective view from a top of the second locking element of FIG. 6.
Figure 8:
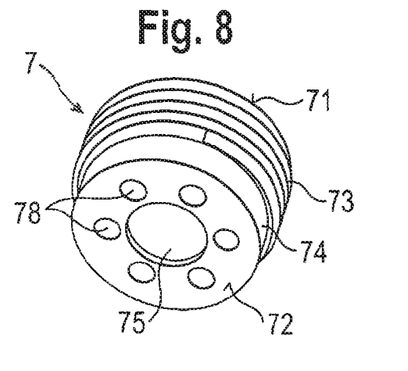
FIG. 8 shows a perspective view from a bottom of the second locking element of FIG. 6.

The second locking element 7 is also substantially cylindrical, and has a first end 71 and an opposite second end 72. Adjacent the first end 71, a portion 73 with an external thread is provided that is configured to cooperate with the internally threaded portion 65 of the first locking element 6. Adjacent the second end 72, a threadless portion 74 is provided. An outer surface of the portion 74 is substantially smooth. An outer diameter of the threadless portion 74 is smaller than an outer diameter of the threaded portion 73. The second locking element 7 further includes a coaxial bore or recess 75, and a coaxial recess 76 adjacent the first end 71 that has an inner diameter that is greater than that of the recess 75. Furthermore, adjacent the first end 71, an engagement structure in the form of a plurality of longitudinal grooves 77 is provided around a central axis C that serve for engagement with an insertion and/or driving tool. The longitudinal grooves 77 may open into a face of the second end 72, forming circular holes 78 therein. The holes 78 can serve for engagement with a tool to mount the second locking element 7 into the first locking element 6 from the second end 62.

Figure 9:
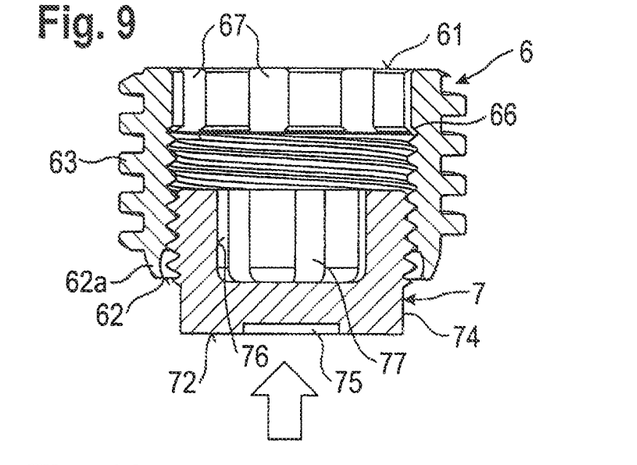
FIGS. 9 to 11 show steps of assembling the locking device according to the first embodiment, in cross-sectional views, the sections being taken in a plane containing a central axis of the locking device.
Figure 10:
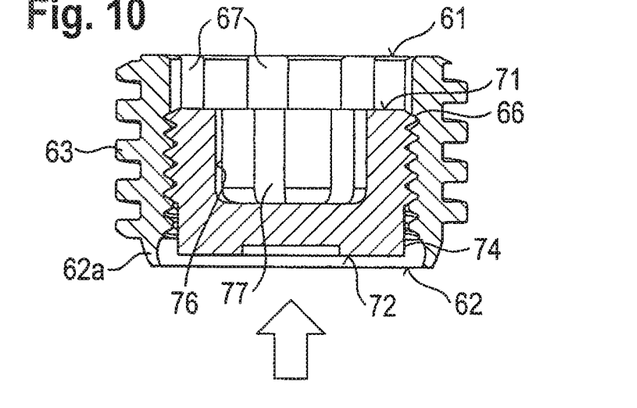
Figure 11:
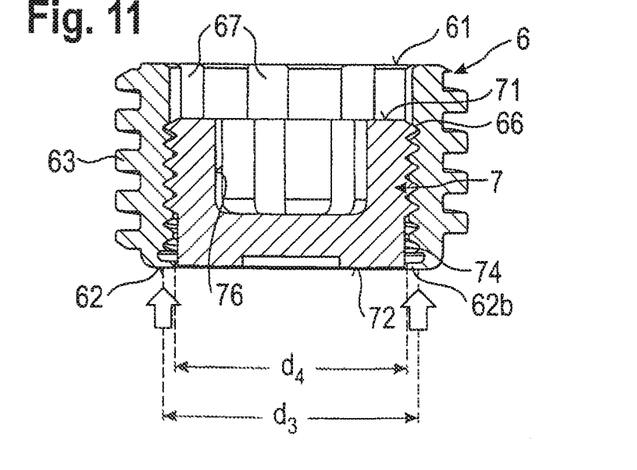

The steps of assembling the first and the second locking elements 6 and 7 will be explained, referring to FIGS. 9 to 11. In a first step, the second locking element 7 is introduced into the first locking element 6 from the second end 62 of the first locking element 6. Then, as shown in FIG. 10, the second locking element 7 is advanced by screwing it in the direction to the first end 61 until the first end 71 of the second locking element 7 abuts against the abutment 66 provided at the coaxial bore of the first locking element 6. A length of the second locking element 7 in an axial direction is such that when the second locking element 7 assumes a first position, wherein its first end 71 abuts against the abutment 66, the second end 72 of the second locking element 7 is located within the concavely rounded hollow cylindrical portion 62a. Thereafter, as shown in FIG. 11, the concavely rounded hollow cylindrical portion 62a is bent inwards, for example, until it nearly touches the threadless portion 74 of the second locking element 7. By this operation, a second stop in the form of an annular abutment 62b is formed. The inner diameter $d_4$ of the annular abutment 62b is smaller than the inner diameter $d_3$ between the roots of the threaded portion 65 of the first locking element 6, but greater than an outer diameter of the threadless portion 74 of the second locking element 7.

All or parts of the polyaxial bone screw, including the locking device, may be made from a biocompatible material. Such biocompatible materials may include, for example, titanium, stainless steel, biocompatible alloys such as titanium nickel alloys, for example Nitinol, or biocompatible plastic materials, such as PEEK (polyetheretherketone). The components can all be made of the same material or of different materials.

Figure 12A:
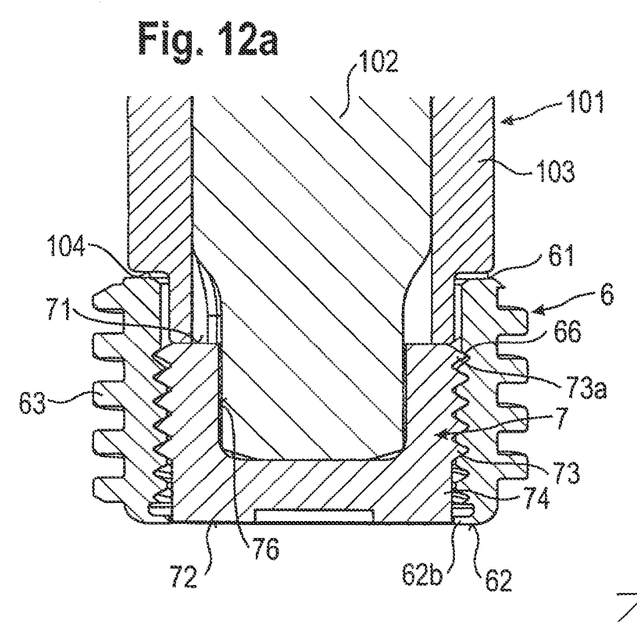
FIG. 12a shows a cross-sectional view of the locking device of the first embodiment with a portion of a tool in a first position, the section being taken in a plane containing the central axis of the locking device.
Figure 12B:
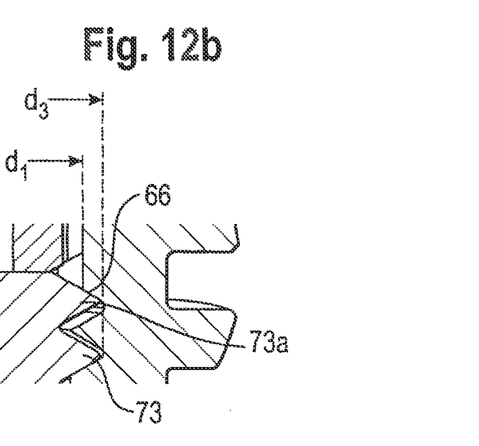

The function or operation of the locking device is shown in FIGS. 12a-13b. In FIG. 12a, a tool 101 is shown that includes an inner drive portion 102 and an outer drive portion 103. The inner drive portion 102 engages the recess 76 and the engagement structure 77 of the second locking element 7. The outer drive portion 103 engages the engagement structure 67 in the first locking element 6. The inner drive portion 102 and the outer drive portion 103 can be rotated independently of one another. By means of the inner drive portion 102, the second locking element 7 can be rotated so that it is advanced towards the first end 61 of the first locking device 6 until, as shown in FIGS. 12a and 12b, a first thread turn 73a adjacent the first end 71 of the second locking element abuts against the abutment 66 formed by the inner wall of the coaxial bore 64. Because the inner diameter $d_1$ of the inner wall of the coaxial bore 64 is smaller than the inner diameter $d_3$ at the root of the internal thread 63 of the first locking element 6, the second locking element 7 cannot advance further towards the first end 61, and is at a first end position at this point. When the second locking element 7 is in the first end position, a gap 104 may be present between the first end 61 of the first locking element 6 and the outer drive portion 103.

Figure 13A:
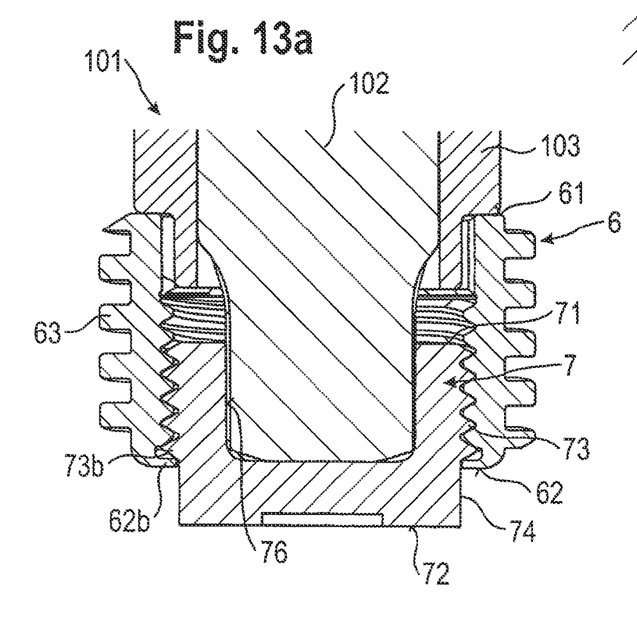
FIG. 13a shows a cross-sectional view of the first embodiment of the locking device with a portion of a tool in a second position, the section being taken in a plane containing the central axis of the locking device.
Figure 13B:
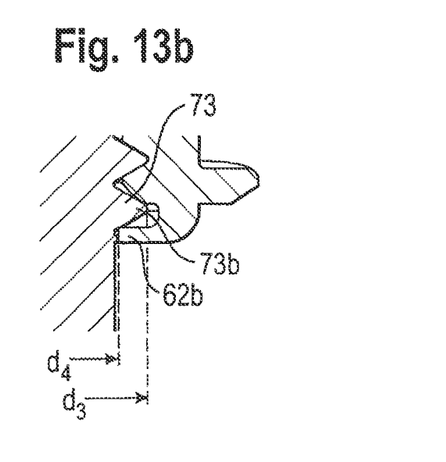

By rotating the first drive portion 102 and by moving down the second drive portion 103 so that it abuts against the first end 61 of the first locking element 6, the second locking element 7 advances in the direction of the second end 62 of the first locking element 6 (i.e., away from the first end 61). The advancement is stopped, when a last thread turn 73b that is on a side of the second locking element 7 opposite the first thread turn 73a abuts against the second stop formed by the annular abutment 62b. Because the inner diameter $d_4$ of the annular abutment 62b is smaller than the inner diameter $d_3$ between the roots of the threaded portion 63 of the first locking element 6, the second locking element 7 can not be screwed further towards the second end 62 or away from the first end 61 and, therefore, can not escape. When the second locking element 7 is in this second end position, the threadless portion 74 projects out of the second end 62 of the first locking element 6.

Figures 14, 15:
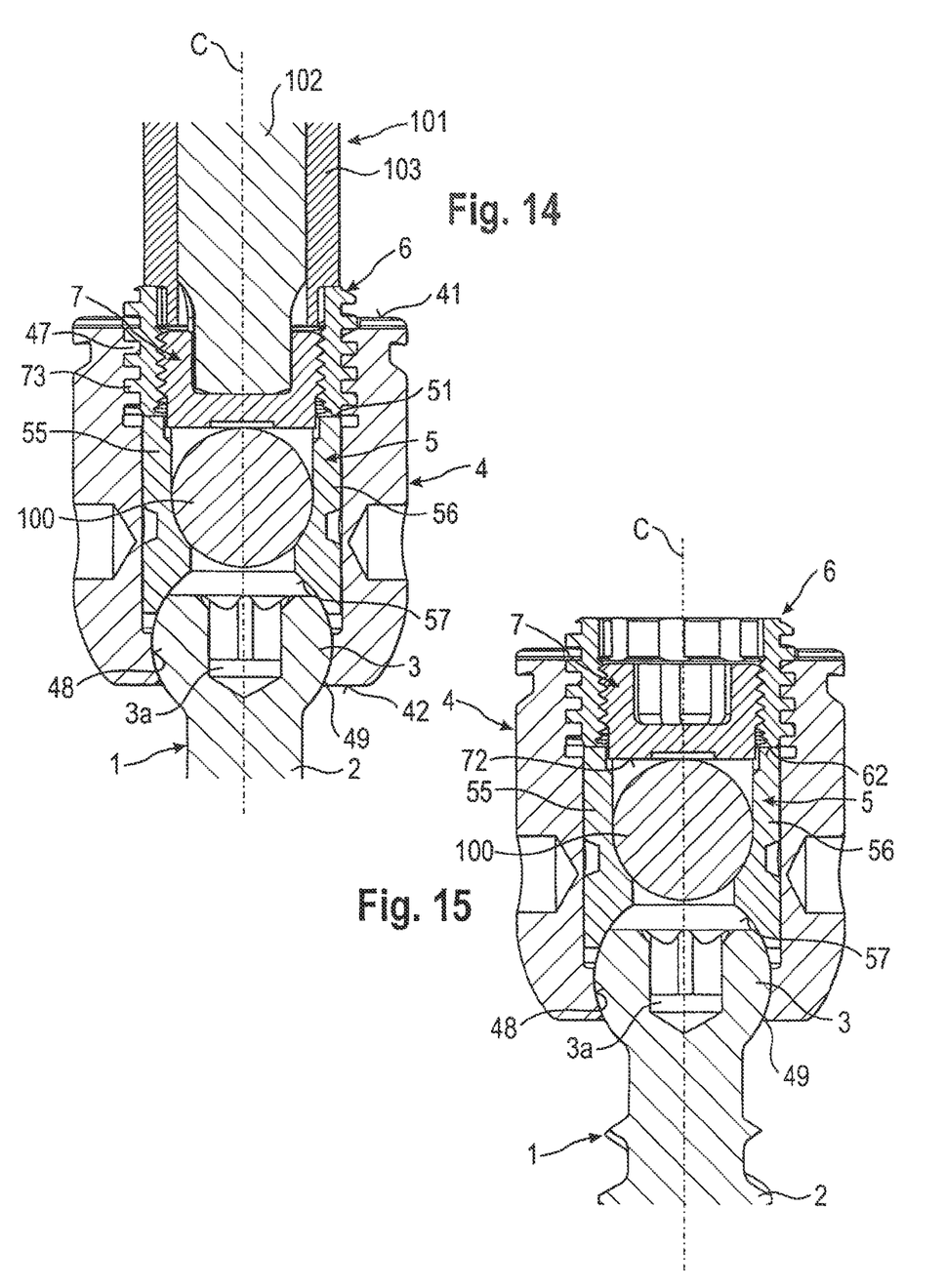
FIG. 14 shows a cross-sectional view of the polyaxial bone screw of FIG. 1 with the locking device according to the first embodiment and a portion of the tool in an assembled state, the section being taken in a plane containing the central axis of the locking device and an axis of a screw element.
FIG. 15 shows a cross-sectional view of the polyaxial bone screw with the locking device according to the first embodiment without the tool.
Figure 16:
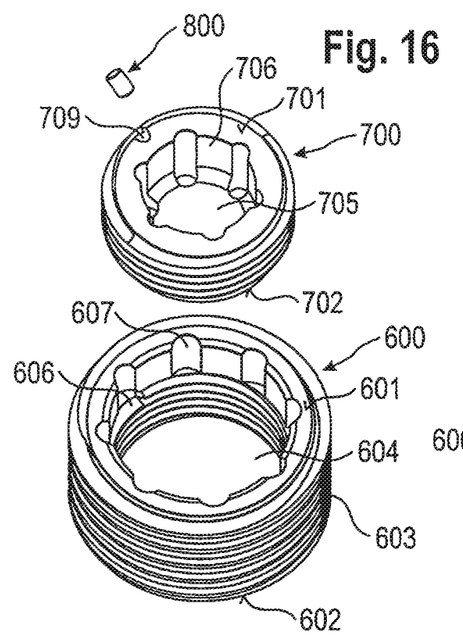
FIG. 16 shows a perspective exploded view of a locking device according to a second embodiment.

The use of the locking device according to the first embodiment is shown in FIGS. 14 and 15. FIG. 14 shows the polyaxial bone screw according to FIGS. 1 and 2 in an assembled state. To allow pivoting before fixation, the receiving part 4 has a seat portion 48, wherein the screw head 3 is held. The seat portion can be spherically-shaped. The screw head 3 and the threaded shank 2 extend through an opening 49 provided at the second end 42 of the receiving part 4. The pressure element 5 is arranged on top of the head 3 and may partially encompass the head 3 with a spherically-shaped recess 57. The pressure element 5 and the receiving part 4 are aligned such that the U-shaped recesses 44, 54 are in alignment, to allow insertion of the rod 100. When the rod 100 rests in the U-shaped recess 54 of the receiving part 5, the legs 55, 56 extend above the rod 100.

The locking device may be inserted into the receiving part 4 in a pre-assembled manner, in which the second locking element 7 is contained in the first locking element 6. With the outer drive portion 103, the first locking element 6 is screwed into the internal thread 47 of the receiving part 4 until its second end 62 abuts against upper free surfaces of the legs 55, 56 of the pressure element 5. By further advancement of the first locking element 6, the pressure element 5 exerts pressure onto the head 3 until the head 3 is finally locked in a desired angular position of the threaded shank 2 relative to the central axis C.

The second locking device 7 is advanced by rotating it with the inner drive portion 102 until the threadless portion 74 extends out of the first locking element 6. Thereby, the second end 72 of the second locking element engages the surface of the rod 100 and presses the rod 100 into the U-shaped recess 54 of the pressure element 5 and/or the U-shaped recess 44 of the receiving part 4. In FIG. 15, the polyaxial bone screw with the locking device is shown without a tool. The first locking element 6 is screwed into the receiving part 4 and presses onto the free legs 55, 56 of the pressure element 5 to lock the head 3. The second locking element 7 presses onto the rod 100 to fix a position of the rod 100 in the channel. The rod 100 and the head 3 of the screw element 1 can be fixed independently from each other, which allows adjustments of the position of the rod 100 while maintaining an angular position of the screw element 1.

During surgery and before insertion of the locking device, the locking device is taken up by or engaged with the tool 101. By an operating error with respect to the tool, it may happen that the second locking element 7 is advanced, even if the locking device is not yet inserted into the receiving part 4. The first and second stops of the first locking element 6 prevent backing out or loss of the second locking element 7 from the first locking element 6. Also, when the locking device has already been inserted into the receiving part 4, subsequent adjustments that require a loosening of the fixation of the rod 100 can be safely performed because the second locking element 7 will abut against the first stop when it is screwed back, for example, by the first drive portion 102. Because the legs 55, 56 of the pressure element 5 extend above the rod 100, when the rod 100 is inserted, the first locking element 6 acts only onto the pressure element 5, and therefore only onto the head 3 and not the rod 100. The second locking element 7 acts only onto the rod 100.

A second embodiment of the locking device is shown in FIGS. 16 to 29. The second embodiment of the locking device can be used with the polyaxial bone screw as described before or with any other bone anchor. The locking device comprises a first locking element 600 and a second locking element 700. The first locking element 600 and the second locking element 700 are connected with the aid of a pin 800. The pin 800 is an abutment member that limits advancement or movement of the second locking member 700 in the first locking member 600.

Figure 20:
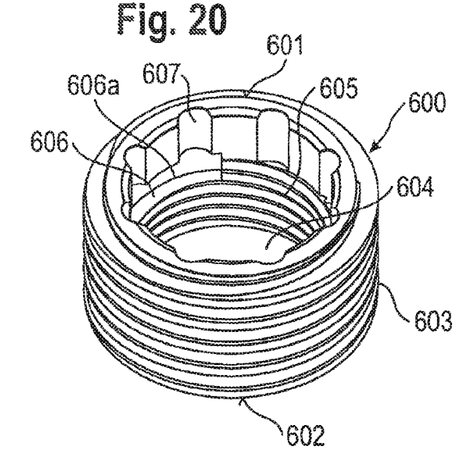
FIG. 20 shows a perspective view from a top of a first locking element of the locking device according to the second embodiment.
Figure 21:
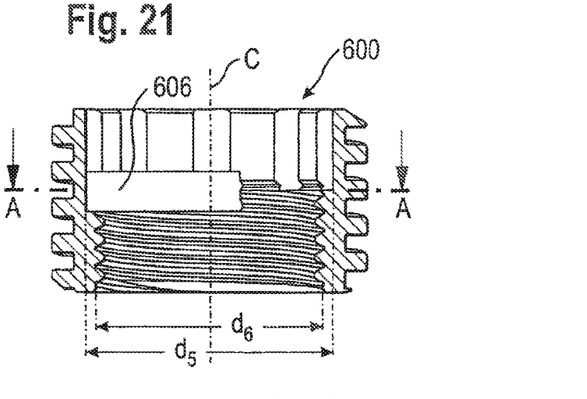
FIG. 21 shows a cross-sectional view of the first locking element of FIG. 20, the section taken in a plane containing a central axis.
Figure 22:
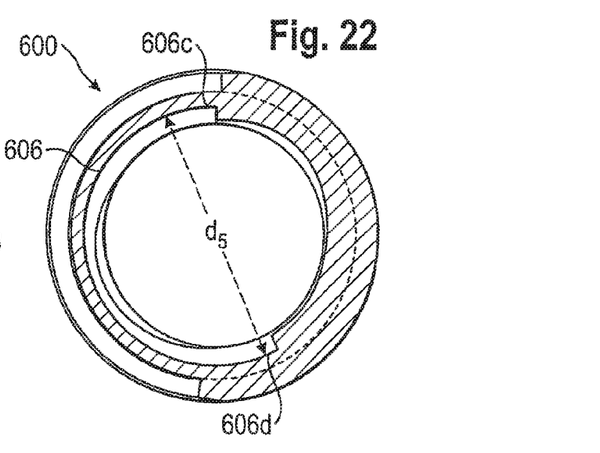
FIG. 22 shows a cross-sectional view along line A-A of the first locking element shown in FIG. 21.
Figure 23:
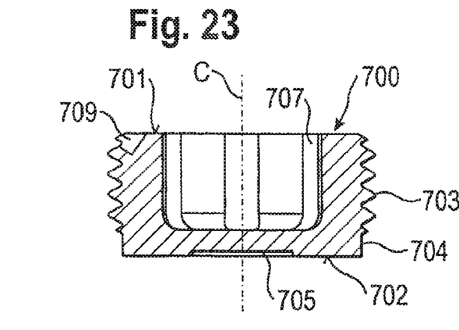
FIG. 23 shows a cross-sectional view of a second locking element of the locking device according to the second embodiment, the section being taken in a plane containing a central axis.
Figure 24:
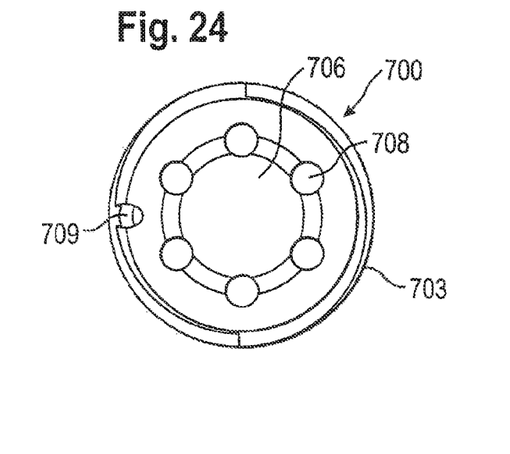
FIG. 24 shows a top view of the second locking element shown in FIG. 23.
Figure 25:
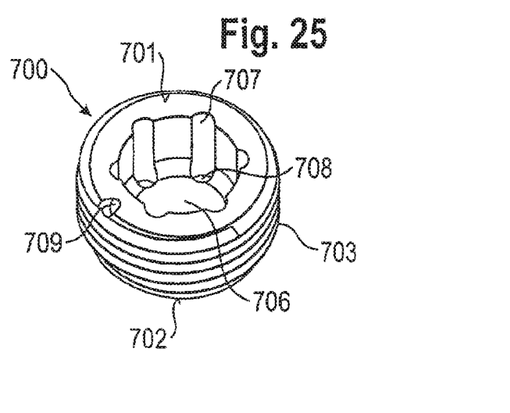
FIG. 25 shows a perspective view of the second locking element of FIG. 23.

Referring first to FIGS. 20 to 22, the first locking member 600 is substantially cylindrical with a first end 601, a second end 602, an external thread portion 603, and a coaxial bore

604. Adjacent the second end 602, an internal thread portion 605 is provided. An engagement structure 607 for engagement with a tool is provided in a region between the internal thread portion 605 and the first end 601. The engagement structure 607 can include extending recesses 607 similar to the first embodiment.

At a transition between the internal thread portion 605 and a portion of the bore 604 with the engagement structure 607, a circumferentially extending groove 606 is provided. The groove 606 may extend in a circumferential direction for slightly more than half a turn or slightly more than a semi-circle, as can be best seen in FIG. 22. An inner diameter $d_5$ of the groove is larger than an inner diameter $d_6$ of the internal thread portion 605 measured between the roots of the internal thread portion 605. A height of the groove 606 in an axial direction corresponds to at least one turn of the internal thread portion 605. By the groove 606, a first stop is provided by one end 606c of the groove 606 in a circumferential direction and a second stop is provided by the other end 606d in a circumferential direction of the groove 606.

The second locking element 700 has a first end 701, an opposite second end 702, and adjacent the first end 701 an externally threaded portion 703. A coaxial bore, i.e., recess 705 extends from the first end 701 in a direction of the second end 702. Adjacent the second end 702, a threadless portion 704 is provided. Adjacent the first end 701, a coaxial recess 706 with an engagement structure in the form of, for example, longitudinal recesses 707 arranged around a central axis C are provided for engagement with a tool. The coaxial engagement recesses 707 extend through the second end 702, thereby providing or forming holes 708. As can be seen in particular in FIGS. 23 to 25, a recess 709 is provided for accommodating the pin 800 seen in FIGS. 16 to 19. The pin 800 is cylindrical and fits into the recess 709 to such an extent that a portion 801 of the pin projects out of the recess 709. The pin 800 may be fixed to the recess. Furthermore, the pin 800 is sized so as to extend into the groove 606 as shown in FIGS. 26 to 29. The pin 800 forms an abutment member that is configured to abut against the first stop formed by one end 606c of the groove 606 and against the second stop formed by the other end 606d of the groove 606.

Figure 17:
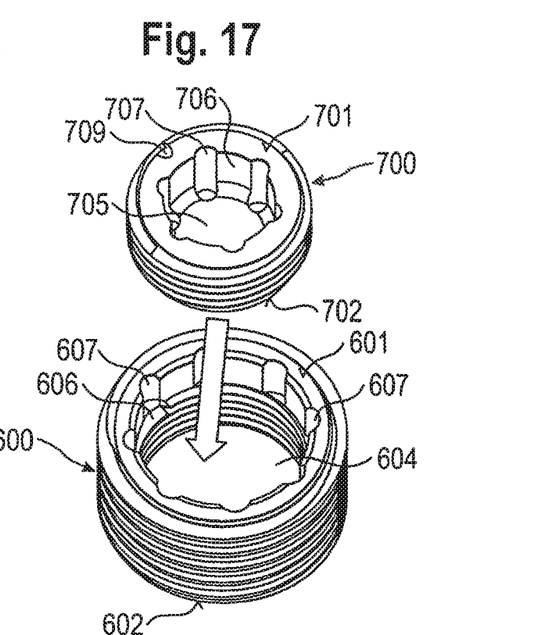
FIGS. 17 to 19 show steps of assembling the locking device according to the second embodiment in a perspective view.
Figure 18:
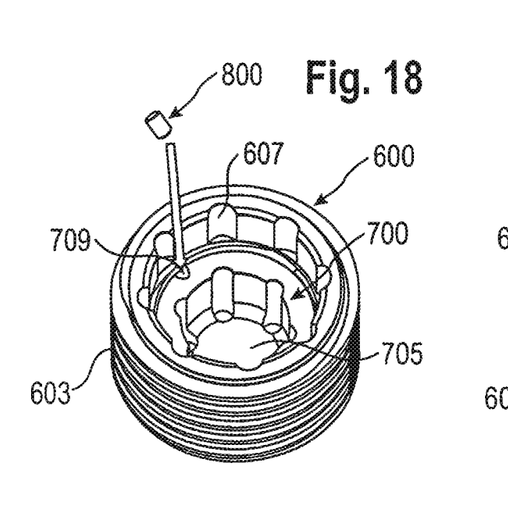
Figure 19:
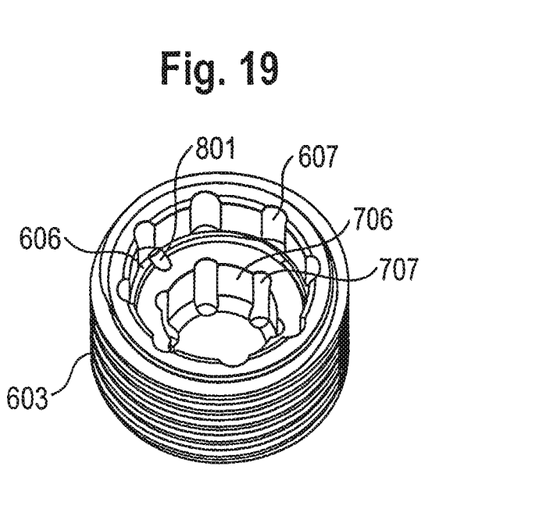

As shown in FIGS. 17 to 19, assembly of the locking device according to the second embodiment is carried out by introducing the second locking member 700 from the first end 601 of the first locking member 600. Once the second locking member 700 is nested into the first locking member 600 by engagement of the respective threads, the second locking member 700 is advanced towards the second end 602 of the first locking member 600 until the recess 709 is positioned at one of the recesses 607 of the engagement structure of the first locking member 600 that is at a position in the region of the groove 606. Then, as shown in FIG. 18, the pin 800 is inserted into the recess 709. Thereafter, the second locking element 700 can be rotated within the boundaries defined by the groove 606.

Figure 26:
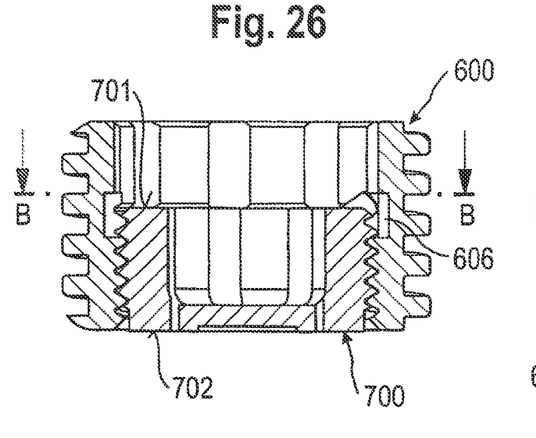
FIG. 26 shows a cross-sectional view of the locking device according to the second embodiment with the second locking element in a first position, the section being taken in a plane containing the central axis of the locking device.
Figure 27:
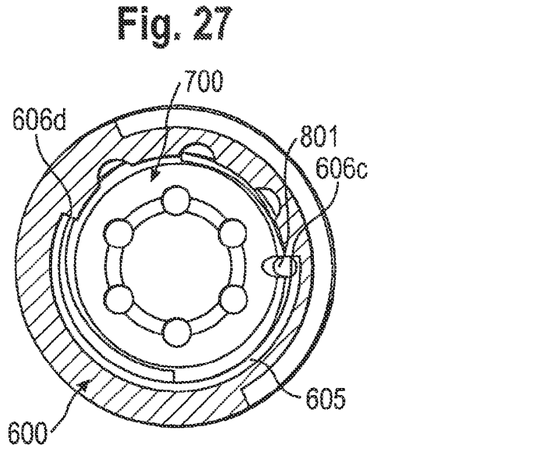
FIG. 27 shows a cross-sectional view of the second locking device shown in FIG. 26 along line B-B of FIG. 26.

The functioning of the second embodiment of the locking device will be explained with reference to FIGS. 26 to 29. In FIG. 26, the second locking element 700 is in a first position. The outwardly projecting portion 801 of the pin 800 abuts against one end 606c of the groove 606. The second end 702 of the second locking element 700 does not project out of the first locking element 600. In this preassembled state, the locking device can be delivered and used during surgery.

Figure 28:
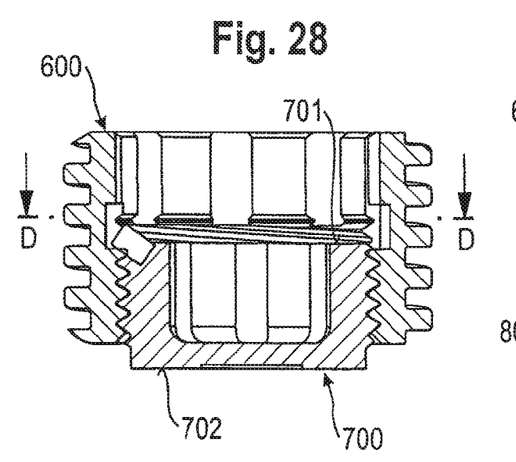
FIG. 28 shows a cross-sectional view of the locking device according to the second embodiment with the second locking element in a second position, the section being taken in a plane containing the central axis of the locking device.
Figure 29:
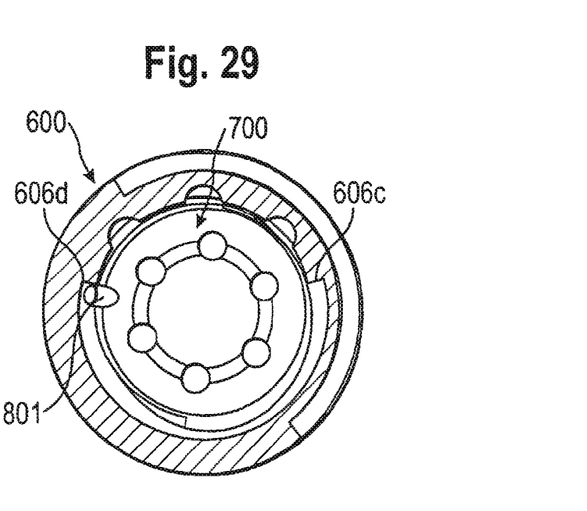
FIG. 29 shows a cross-sectional view of the locking device of FIG. 28 along line D-D of FIG. 28.
Figures 30, 31:
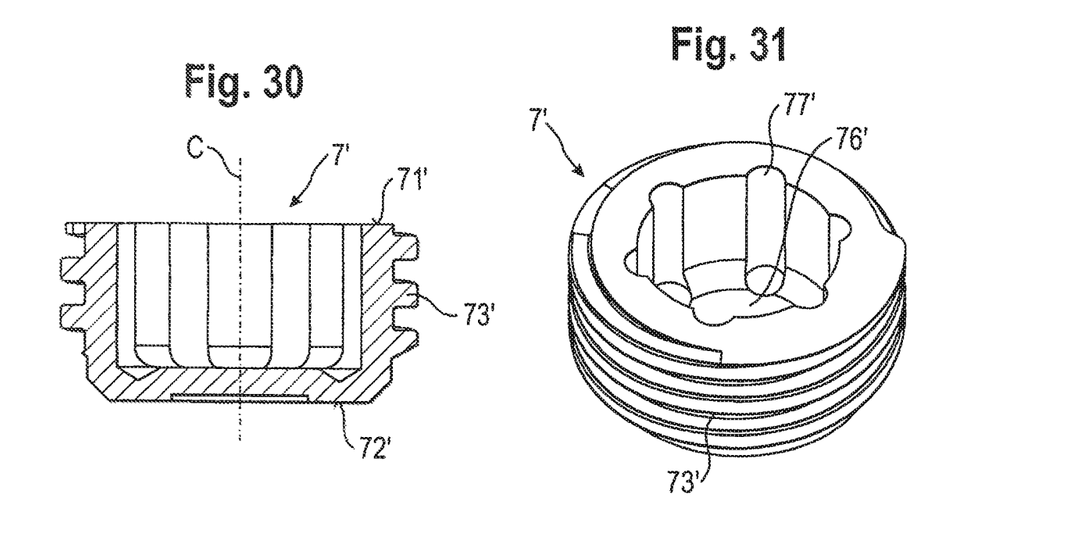
FIG. 30 shows a cross-sectional view of the second locking element according to a further modified embodiment.
FIG. 31 shows a perspective view from a top of the second locking element of FIG. 30.
Figure 32:
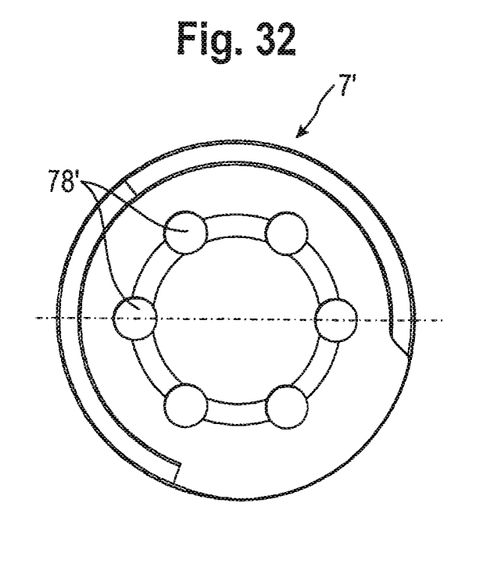
FIG. 32 shows a top view of the second locking element of FIG. 30.
Figure 33:
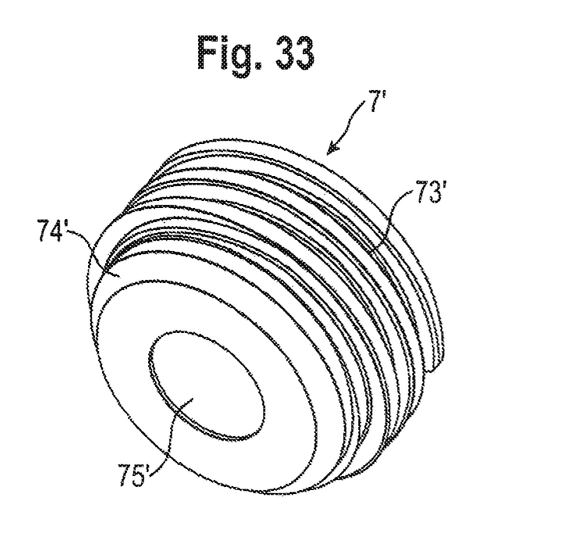
FIG. 33 shows a perspective view from the bottom of the second locking element of FIG. 30.

In FIG. 28, the second locking element 700 has been rotated and advanced downward until the outwardly projecting portion 801 of the pin 800 abuts against the other end 606d of the groove 606. In this position, the second locking element 700 can no longer be advanced downward and therefore is prevented from backing out or escaping out of the first locking element 600. A length of the threadless portion 704 in an axial direction is such that in the second position, shown in FIG. 28, a portion of the second locking element 700 that projects outward from the first locking element 600 is suitable for pressing onto the rod 100 and fixing the rod 100.

As in the first embodiment, the external threaded portion 603 of the first locking element 600 can have any thread form, but preferably has a thread form that prevents splaying of the legs of a corresponding receiving part, in particular, a flat thread as shown, or a negative angle thread. The internal thread 605 of the first locking element 600 and the cooperating external thread 703 of the second locking element 700 may have a metric thread form or may also have a flat thread form, among others.

The materials of the parts and components of the locking device according to the second embodiment may be the same or similar to those of the first embodiment.

The second locking element 700 may also be introduced into the first locking element 600 from the second end 602. Since the second stop of the locking device in the second embodiment is located approximately in the middle of the first locking element 600 in an axial direction, the locking device according to the second embodiment can be designed to be more compact.

In a further modified embodiment, the first locking element 6' includes an internal flat thread 63' and the second locking element 7' includes an external flat thread 73' as can be seen from FIGS. 30 to 35b. The thread form is the only difference between the first locking elements and the second locking elements according to the first embodiment and this further modified embodiment.

Figures 34A, 34B, 35A, 35B:
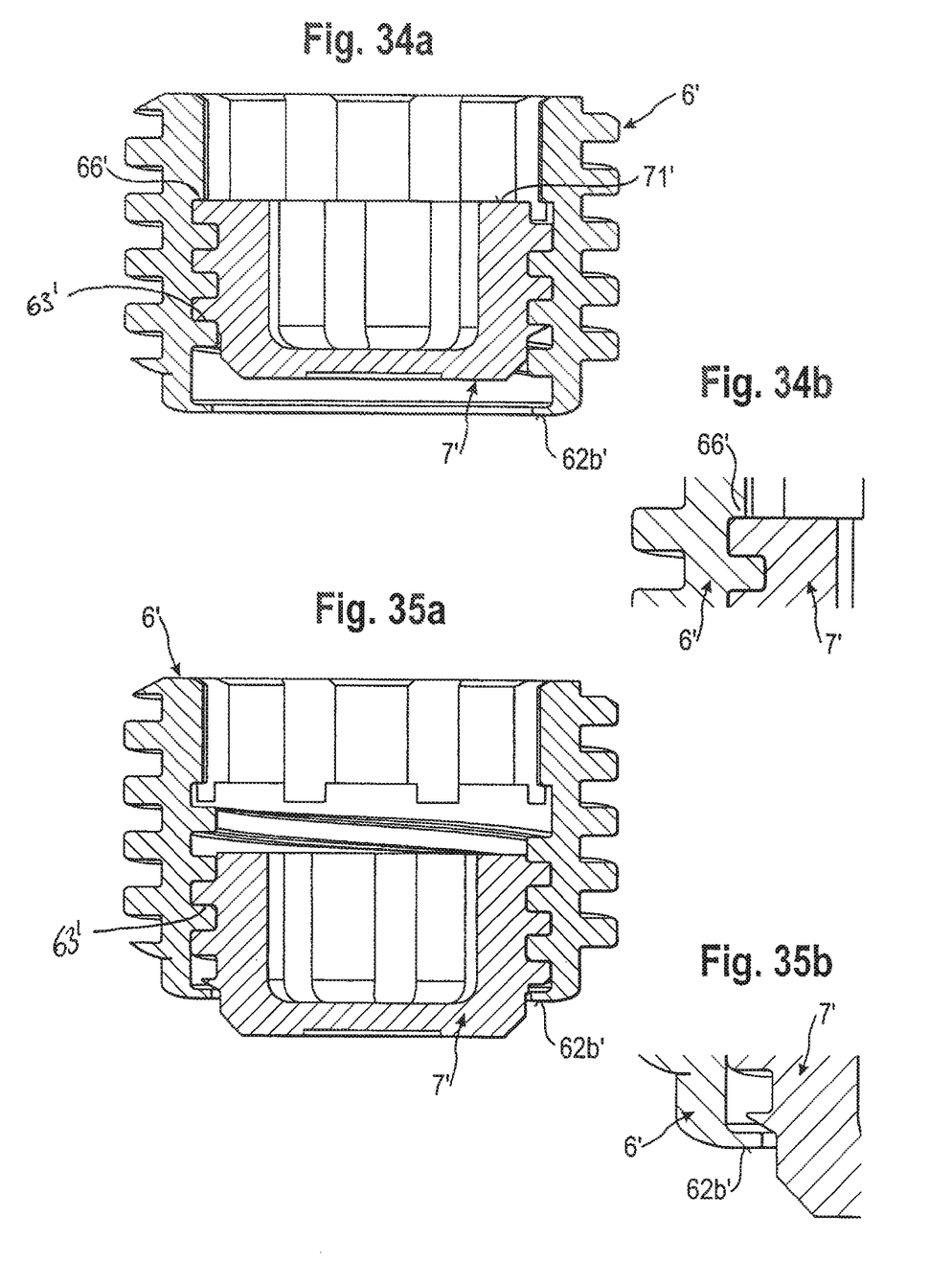

FIGS. 34a and 34b show the second locking element 7' abutting against the abutment 66' with its first end 71'.

FIGS. 35a and 35b show the second locking element 7' abutting against the annular abutment 62h' with a portion of thread 73' on a side opposite first end 71'.

With respect to the second embodiment, a modification to include the above mentioned flat thread configuration is also possible.

One advantage of the flat thread configuration, referring to the inner thread of the first locking element 6' and the outer thread of the second locking element 7' is that proper end stops are defined, because a flat thread is more robust and does not have sharp edges, which could violate an integral structure of the end stops. Because of the robust design of the flat threads, smaller dimensioning may be possible. This effect may also be intensified since no radial forces have to be taken up within the flat thread.

Further modifications of the embodiments described are also conceivable. A locking device according to embodiments of the invention can also be used with a monoaxial screw or with a bone plate. For example, the locking device can be used with a monoaxial screw and a rod that is made from an elastomeric material, which is used for dynamic stabilization.

The second locking element may have engagement structures at its second end that faces the rod, such as projections to enhance engagement with the rod.

Further, the engagement structures in the first and second locking element are not limited to the described grooves. They can have any other shape. Alternatively, an engagement structure at the surface of the first ends of the first and/or second locking element may be provided.

Other constructions of the stops for limiting the movement of the second locking element in the first locking element are also conceivable. For example, the first locking element may have an abutment member that abuts in a groove of the second locking member.

The independent head and rod fixation can also be realized by other means. For example, the pressure element can be shaped differently without legs that extend above the rod. In this case, the first locking element may have a structure at its second end that presses onto such a pressure element.

The polyaxial bone anchor can also be realized in many different known manners that are configured to engage with the locking device, for example, a polyaxial bone anchor with a favored angle bottom configuration, or with a bottom loader configuration.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A locking device for securing a rod-shaped element in a receiving part of a bone anchor, the locking device comprising:
   a first locking member comprising a first end, a second end, a central axis passing through the first end and the second end, an outer surface with an external thread, a coaxial bore passing through the first locking member, and an internal thread provided along at least a portion of the bore; and
   a second locking member comprising a first end, a second end, and an outer surface with an external thread configured to cooperate with the internal thread of the first locking member,
   wherein when the second locking member is positioned in the first locking member, the second locking member is movable along the central axis by rotating the second locking member relative to the first locking member, wherein movement of the second locking member is limited towards the first end of the first locking member by a first stop and towards the second end of the first locking member by a second stop, and wherein at least one of the first stop or second stop is arranged in the bore of the first locking member.

2. The locking device of claim 1, wherein when the first and second locking members are in an assembled state, the first and second locking members are inseparable.

3. The locking device of claim 1, wherein when the second locking member is in a first position where the first and second locking members are in contact at the first stop, the first end of the second locking member faces the first end of the first locking member and is positioned within the bore of the first locking member.

4. The locking device of claim 1, wherein when the second locking member is in a second position where the first and second locking members are in contact at the second stop, at least a portion of the second locking member protrudes outside of the bore of the first locking member.

5. The locking device of claim 1, wherein the first locking member has an engagement structure at the first end of the first locking member and extending into the bore of the first locking member for engagement with a tool.

6. The locking device of claim 1, wherein the first stop is positioned at a distance from the first end of the first locking member.

7. The locking device of claim 1, wherein the first stop comprises an abutment provided on the first locking member.

8. The locking device of claim 1, wherein the first stop comprises an inner surface portion along the bore of the first locking member, and wherein a diameter of the bore at the first stop is equal to or less than an inner diameter between roots of the internal thread of the first locking member.

9. The locking device of claim 1, wherein the second stop comprises an abutment at the second end of the first locking member.

10. The locking device of claim 1, wherein the second stop comprises a projection that projects into the bore to be closer to the central axis than a root of the internal thread of the first locking member.

11. The locking device of claim 10, wherein the projection is annular.

12. The locking device of claim 1, wherein the second stop comprises an abutment positioned at a distance from the first end and the second end of the first locking member.

13. The locking device of claim 12, wherein the first stop comprises a first end of a groove in an inner wall that defines the bore of the first locking member.

14. The locking device of claim 13, wherein the abutment of the second stop comprises a second end of the groove.

15. The locking device of claim 14, wherein the groove extends circumferentially relative to the first locking member.

16. The locking device of claim 15, wherein the groove extends on the first locking member for one half turn or more around the central axis.

17. The locking device of claim 12, wherein the second locking member comprises an abutment member configured to project into a groove of the first locking member.

18. The locking device of claim 17, wherein the abutment member comprises a pin.

19. The locking device of claim 1, wherein the coaxial bore passes entirely through the first locking member.

20. A bone anchor comprising:
   an anchoring element comprising a shank to be anchored in a bone or a vertebra;
   a receiving part configured to be connected to the shank, the receiving part comprising:
      a first end opposite to the shank and a second end facing the shank when the anchoring element and the receiving part are assembled;
      a longitudinal axis passing through the first and second ends;
      a bore coaxial with the longitudinal axis and extending from the first end of the receiving part through at least a portion of the receiving part; and
      a substantially U-shaped recess for receiving a rod-shaped element, the recess defining two free legs extending in a direction of the first end of the receiving part, wherein the legs are provided with an internal thread; and
   a locking device comprising:
      a first locking member comprising a first end, a second end, an outer surface with an external thread configured to engage the internal thread of the legs, a coaxial bore passing through the first locking member, and an internal thread provided along at least a portion of the bore of the first locking member; and
      a second locking member comprising a first end, a second end, and an outer surface with an external thread configured to engage the internal thread of the first locking member;
      wherein when the second locking member is positioned in the first locking member, the second locking member is movable by rotating the second locking member relative to the first locking member, and wherein movement of the second locking member is limited towards the first end of the first locking member by a first stop and towards the second end of the first locking member by a second stop, and wherein at least one of the first stop or second stop is arranged in the bore of the first locking member.

21. The bone anchor of claim 20, wherein the anchoring element further comprises a head, and wherein the receiving part comprises a region adjacent to the second end of the receiving part for pivotably receiving the head.

22. The bone anchor of claim 21, further comprising a pressure element configured to be arranged in the receiving part between the head and the locking device for exerting pressure onto the head to lock the head in the receiving part.

23. An assembly comprising the bone anchor of claim 21 and a rod-shaped element, wherein when the bone anchor is in an assembled state and the rod-Shaped element is inserted into the U-shaped recess, the first locking member is configured to lock the head relative to the receiving part without fixing a position of the rod-shaped element relative to the receiving part, and wherein the second locking member is configured to fix the position of the rod-shaped element relative to the receiving part.

24. A method of coupling a rod to a bone anchor, the bone anchor comprising an anchoring element, a receiving part configured to be connected to the anchoring element and comprising a first end, a second end, a longitudinal axis passing through the first and second ends, a bore coaxial with the longitudinal axis and configured to receive a head of the anchoring element, and a substantially U-shaped recess for receiving the rod, the recess defining two free legs provided with an internal thread, and a locking device comprising a first locking member comprising a first end, a second end, an outer surface with an external thread configured to engage the internal thread of the legs, a coaxial bore passing through the first locking member, and an internal thread provided along at least a portion of the bore of the first locking member, and a second locking member comprising a first end, a second end, and an outer surface with an external thread configured to engage the internal thread of the first locking member; wherein when the second locking member is positioned in the first locking member, the second locking member is movable by rotating the second locking member relative to the first locking member, wherein movement of the second locking member is limited towards the first end of the first locking member by a first stop and towards the second end of the first locking member by a second stop, and wherein at least one of the first stop or second stop is arranged in the bore of the first locking member, the method comprising:
- introducing a head of the anchoring element into the bore of the receiving part;
- inserting the anchoring element into a bone or vertebra;
- adjusting the receiving part relative to the anchoring element;
- inserting the rod into the recess of the receiving part;
- advancing the locking device including the first locking member and the second locking member in the recess to lock a position of the anchoring element relative to the receiving part; and
- advancing the second locking member relative to the first locking member to lock a position of the rod relative to the bone anchor.

25. The method of claim 24, wherein the bone anchor further comprises a pressure element configured to be inserted between the anchoring element and the rod, and wherein advancing the first locking member exerts pressure on the pressure element and advancing the second locking member exerts pressure on the rod.

26. The method of claim 24, further comprising:
- inserting the second locking member into the bore of the first locking member; and
- adjusting the first locking member and the second locking member to prevent escape of the second locking member from either the first end or the second end of the first locking member.

27. The method of claim 26, wherein adjusting the first locking member comprises reducing a diameter of an opening at the second end of the first locking member.

28. The method of claim 26, wherein the first locking member has a groove in an inner wall defining the bore of the first locking member, and wherein adjusting the second locking member comprises attaching a pin to the second locking member to abut against sides of the groove.

* * * * *